(12) United States Patent
Wang

(10) Patent No.: US 11,232,717 B2
(45) Date of Patent: Jan. 25, 2022

(54) VOCALIZATION APPLIANCE FOR ASSISTING VOCAL CORD CLOSURE TRAINING

(71) Applicant: Yaxian Liu, Beijing (CN)

(72) Inventor: Feng Wang, Beijing (CN)

(73) Assignee: Yaxian Liu, Beijing (CN)

( * ) Notice: Subject to any disclaimer, the term of this patent is extended or adjusted under 35 U.S.C. 154(b) by 282 days.

(21) Appl. No.: 16/581,765

(22) Filed: Sep. 25, 2019

(65) Prior Publication Data

US 2020/0074885 A1  Mar. 5, 2020

(30) Foreign Application Priority Data

Oct. 19, 2018  (CN) .......................... 201811224559.7

(51) Int. Cl.
*G09B 19/04* (2006.01)
*A61B 13/00* (2006.01)

(52) U.S. Cl.
CPC .............. *G09B 19/04* (2013.01); *A61B 13/00* (2013.01)

(58) Field of Classification Search
CPC ................................. G09B 19/04; A61B 13/00
USPC .......................................................... 434/185
See application file for complete search history.

(56) References Cited

U.S. PATENT DOCUMENTS

| | | | | |
|---|---|---|---|---|
| D160,490 S | * | 10/1950 | Name not available | .... D24/136 |
| 2,549,398 A | * | 4/1951 | Stelz | ......................... A61F 5/58 |
| | | | | 600/24 |
| 3,014,286 A | * | 12/1961 | Hricak | ................... G09B 19/06 |
| | | | | 434/157 |
| 3,556,093 A | * | 1/1971 | Quick | ........................ A61F 5/58 |
| | | | | 600/24 |
| 3,867,770 A | * | 2/1975 | Davis | ..................... G09B 19/04 |
| | | | | 434/185 |
| 4,112,596 A | * | 9/1978 | Fletcher | ............... A61B 5/0534 |
| | | | | 600/590 |
| 4,718,662 A | * | 1/1988 | North | ................... A63B 23/032 |
| | | | | 128/860 |
| 5,213,553 A | * | 5/1993 | Light | ........................ A61F 5/58 |
| | | | | 434/185 |
| 5,257,930 A | * | 11/1993 | Blakeley | ................ G09B 19/04 |
| | | | | 433/168.1 |
| 5,401,234 A | * | 3/1995 | Libin | ........................ A61F 5/01 |
| | | | | 128/861 |
| 5,645,420 A | * | 7/1997 | Bergersen | ................ A61C 7/08 |
| | | | | 433/6 |

(Continued)

*Primary Examiner* — Jack Yip

(57) ABSTRACT

A vocalization appliance for assisting vocal cord closure training includes: an inner arc plate, an outer arc plate, and two partitions which are oppositely disposed, wherein the inner arc plate is opposite to the outer arc plate, and the two partitions are placed with an interval between the inner arc plate and the outer arc plate; the two partitions, the inner arc plate and the outer arc plate are enclosed to form an accommodating cavity, and the accommodating cavity is separated into an upper accommodating room and a lower accommodating room along a height direction; the upper accommodating room accommodates upper incisors while the lower accommodating room accommodates lower incisors; opposite side ends of the inner arc plate respectively extend away from the accommodating cavity, and opposite side ends of the outer arc plate also respectively extend away from the accommodating cavity, thereby separating mouth corners.

23 Claims, 4 Drawing Sheets

(56) References Cited

U.S. PATENT DOCUMENTS

| | | | | |
|---|---|---|---|---|
| 5,689,246 A * | 11/1997 | Dordick | ............... | A61F 4/00 |
| | | | | 340/4.11 |
| 5,735,772 A * | 4/1998 | Schiavoni | ............ | A63B 23/032 |
| | | | | 433/69 |
| 5,876,199 A * | 3/1999 | Bergersen | ............ | A61C 7/08 |
| | | | | 433/6 |
| 6,510,853 B1 * | 1/2003 | Kittelsen | ............ | A63B 71/085 |
| | | | | 128/859 |
| 6,761,699 B2 * | 7/2004 | Chahine | ............ | A61H 39/00 |
| | | | | 601/134 |
| 7,214,064 B1 * | 5/2007 | Hall | ............ | G09B 19/04 |
| | | | | 434/185 |
| 10,111,729 B1 * | 10/2018 | Lowe | ............ | A61C 7/008 |
| 2004/0038188 A1 * | 2/2004 | Lee | ............ | G09B 19/04 |
| | | | | 434/185 |
| 2014/0220520 A1 * | 8/2014 | Salamini | ............ | A61B 5/7455 |
| | | | | 434/185 |
| 2014/0370465 A1 * | 12/2014 | Lucas | ............ | A61C 7/36 |
| | | | | 433/214 |
| 2015/0031940 A1 * | 1/2015 | Floyd | ............ | A61F 5/58 |
| | | | | 600/24 |
| 2018/0169504 A1 * | 6/2018 | Williams | ............ | A61F 5/566 |
| 2020/0215384 A1 * | 7/2020 | Farrell | ............ | A61F 5/566 |

\* cited by examiner

VOCALIZATION APPLIANCE FOR ASSISTING VOCAL CORD CLOSURE TRAINING

CROSS REFERENCE OF RELATED APPLICATION

The present invention claims priority under 35 U.S.C. 119(a-d) to CN 201811224559.7, filed Oct. 19, 2018.

BACKGROUND OF THE PRESENT INVENTION

Field of Invention

The present invention relates to a technical field of vocal cord closure correction, and more particularly to a vocalization appliance for assisting vocal cord closure training.

Description of Related Arts

Vocal cord is a major component of vocal organs. The vocal cords are located in the middle of the larynx and have a bilaterally symmetrical structure. The sagittal fissure between the vocal cords on both sides is a rima glottidis. During vocalizing, the vocal cords on both sides are tightened, and the rima glottidis is shrunk, or even closed. As a result, airflow from the trachea and lungs continuously impacts the vocal cords, causing vibration and vocalization.

When the sound is abnormal in terms of sound quality, volume, pitch or duration, vocalization needs to be corrected by means of an auxiliary device. During conventional speech vocal correction process, the vocal cord closure training is usually assisted by an appliance. The appliance includes a first fixing cavity and a second fixing cavity disposed opposite to each other, and the first fixing cavity and the second fixing cavity are respectively used for fixing the upper row of incisors and the lower row of incisors, so as to maintain a certain distance between the upper and lower teeth to provide a positive effect on vocal correction. Further research has found that the above-mentioned appliance has limited correction effect on vocal dysfunctions caused by vocal cord closure, such as vocal cord paralysis, lack of vocal cord closure ability, and poor vocal cord closure. It is difficult to achieve healthy pronunciation and speech resonance.

Therefore, there is a need for an appliance for assisting vocal cord closure training, so as to solve the above problems.

SUMMARY OF THE PRESENT INVENTION

In view of the above problems, an object of the present invention is to provide a vocalization appliance for assisting vocal cord closure training. After wearing, a distance between two sides of a mouth is enlarged and extended, corners of the mouth is supported and separated, and the vocal cords are passively closed, which helps to achieve healthy pronunciation and voice resonance.

Accordingly, in order to accomplish the above object, the present invention provides a vocalization appliance for assisting vocal cord closure training, comprising: an inner arc plate, an outer arc plate, and two partitions which are oppositely disposed, wherein the inner arc plate is opposite to the outer arc plate, and the two partitions are placed with an interval between the inner arc plate and the outer arc plate; the two partitions, the inner arc plate and the outer arc plate are enclosed to form an accommodating cavity, and the accommodating cavity is separated into an upper accommodating room and a lower accommodating room along a height direction; the upper accommodating room accommodates upper incisors while the lower accommodating room accommodates lower incisors; opposite side ends of the inner arc plate respectively extend away from the accommodating cavity, and opposite side ends of the outer arc plate also respectively extend away from the accommodating cavity, thereby separating mouth corners.

Preferably, the vocalization appliance further comprises: a tongue depressor disposed on a side surface of the inner arc plate facing away from the outer arc plate, wherein the tongue depressor extends away from the outer arc plate.

Preferably, a width of the tongue depressor gradually increases towards the inner arc plate.

Preferably, the tongue depressor comprises a connected end and a free end which are oppositely disposed, wherein the connected end is disposed on the inner arc plate opposite to the lower accommodating room, and the free end extends towards the upper accommodating room.

Preferably, an upper end surface of the outer arc plate extends upwardly to form an upper baffle, and a lower end surface of the outer arc plate extends downwardly to form a lower baffle; the upper baffle prevent an inner surface of an upper lip from contacting upper teeth, and the lower baffle prevents an inner surface of a lower lip from contacting lower teeth.

Preferably, an upper groove for accommodating an upper lip ligament is provided at a middle of the upper baffle, and the upper baffle smoothly transitions from opposite sidewalls of the upper groove to the upper end face at both sides; a lower groove for accommodating a lower lip ligament is provided at a middle of the lower baffle, and the lower baffle smoothly transitions from opposite sidewalls of the lower groove to the lower end face at both sides.

Preferably, both end portions of the inner arc plate are first end portions, and the first end portions extend from a joint of the inner arc plate and the partitions towards canines; both end portions of the outer arc plate are second end portions, and the second end portions extend from a joint of the outer arc plate and the partitions towards molars.

Preferably, gaps are reserved between the first end portions of the inner arc plate and the second end portions of the outer arc plate, and widths of the gaps gradually, increase backwards the accommodating cavity.

Preferably, each of the first end portions of the inner arc plate comprises a first upper side surface, a first end surface, and a first lower side surface, wherein smooth transition is provided between the first upper side surface, the first end surface, and the first lower side surface; each of the second end portions of the outer arc plate comprises a second upper side surface, a second end surface, and a second lower side surface, wherein smooth transition is provided between the second upper side surface, the second end surface, and the second lower side surface; slits are respectively provided at a middle of the second upper side, a middle of the second end surface, and a middle of the second lower side.

Furthermore, preferably, the vocalization appliance is made of a rubber foam material.

It can be seen from the above description that the vocalization appliance for assisting vocal cord closure training of the present invention has the following advantages compared with the prior art: the upper accommodating room and the lower accommodating room respectively fix the upper incisors and the lower incisors, so that an interval is maintained between the upper teeth and the lower teeth; the opposite ends of the inner arc plate and the opposite ends of the outer arc plate all extend away from the accommodating cavity for separating the upper lip from the lower lip, and keeping the lips and muscles relaxed; increasing a distance between the opposite sides of the mouth helps to increase resonance and promote passive and healthy closure of the vocal cords; as a result, the muscles and nerves, that help the vocal cords close, can be maximally stretched and exercised, which helps to achieve healthy pronunciation, fully resonate sinus and frontal sinus, and produce a voice resonance; the outer arc plate extends from inside of the lips to outside of the lips to keep separating the mouth corners, while avoid a bad habit of actively opening the mouth during vocalization.

BRIEF DESCRIPTION OF THE DRAWINGS

Embodiments of the present invention will be described below with reference to the accompanying drawings, and the above features and technical advantages of the present invention will become more apparent and understood.

ELEMENT REFERENCE

Figure 1:
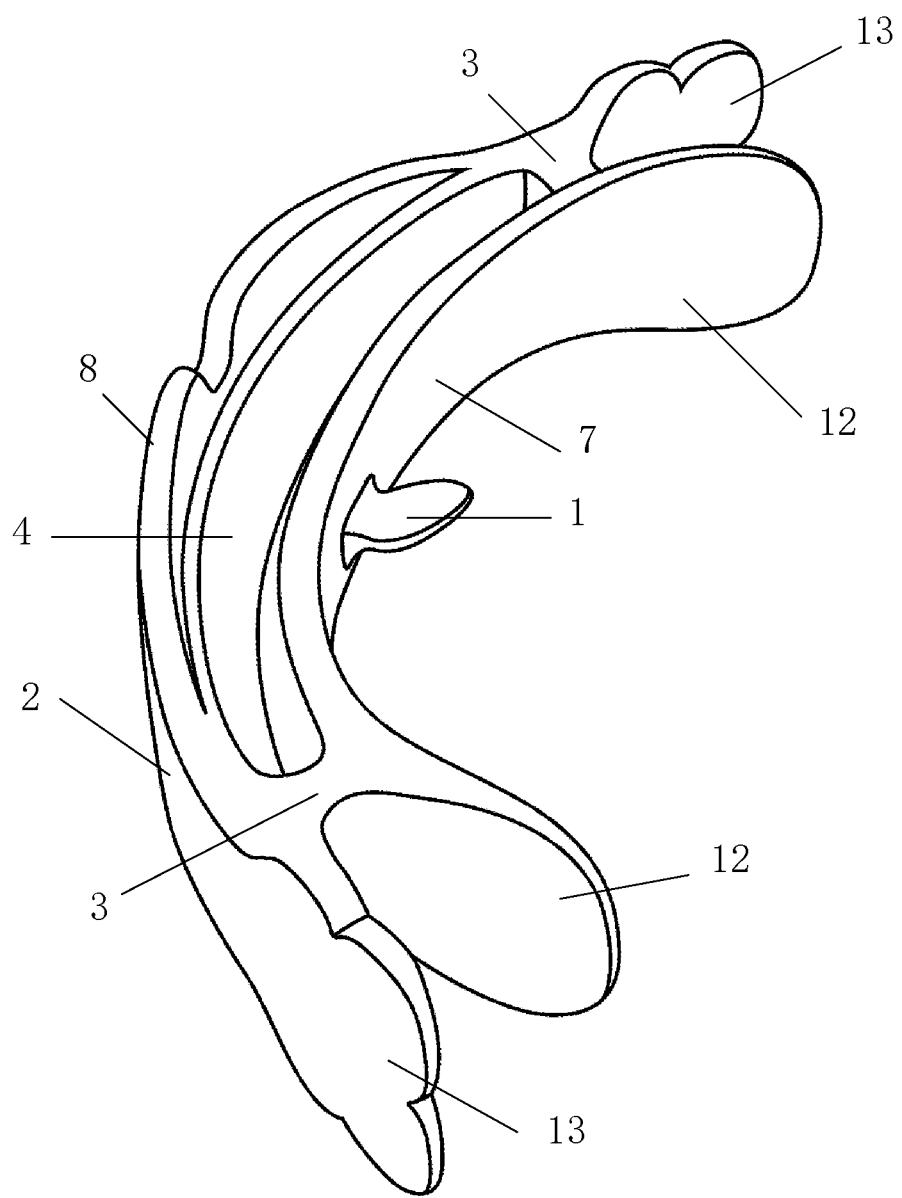
FIG. 1 is a sketch view of a vocalization appliance for assisting vocal cord closure training according to an embodiment of the present invention.

1: inner arc plate; 2: outer arc plate; 3: partition; 4: accommodating cavity; 5: upper accommodating room; 6: lower accommodating room; 7: tongue depressor; 8: upper baffle; 9: lower baffle; 10: upper groove; 11: lower groove; 12: first end portion; 13: second end portion; 14: gap; 15: incisor; 16: canine; 17: molar; 18: tongue; 19: upper lip; 20: lower lip.

DETAILED DESCRIPTION OF THE PREFERRED EMBODIMENT

In order to make the objects, technical solutions and advantages of the present invention more apparent, the present invention will be further described in detail below in conjunction with the specific embodiment and with reference to the accompanying drawings, wherein the same components are denoted by the same reference number. It is to be noted that the terms "front", "back", "left", "right", "upper" and "lower" as used in the following description refer to the directions in the drawings, and the terms "inner" and "outer" are used to refer to a direction toward or away from the geometric center of a particular component, respectively.

Figure 2:
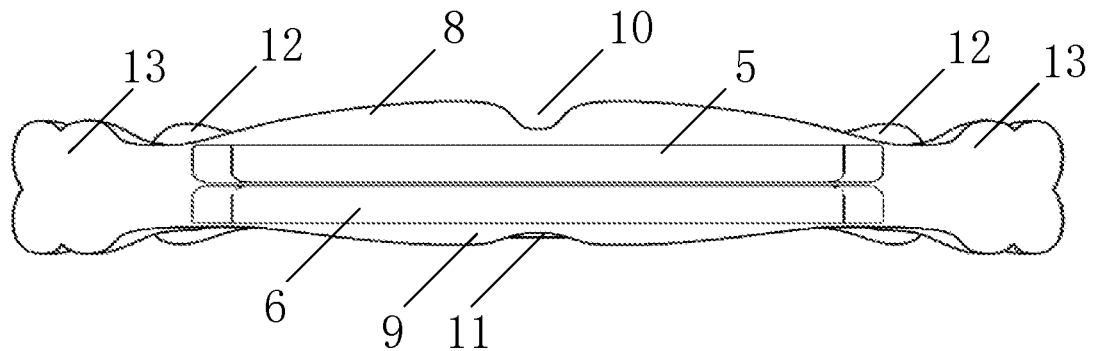
FIG. 2 is a front view of the vocalization appliance for assisting the vocal cord closure training as shown in FIG. 1.
Figure 3:
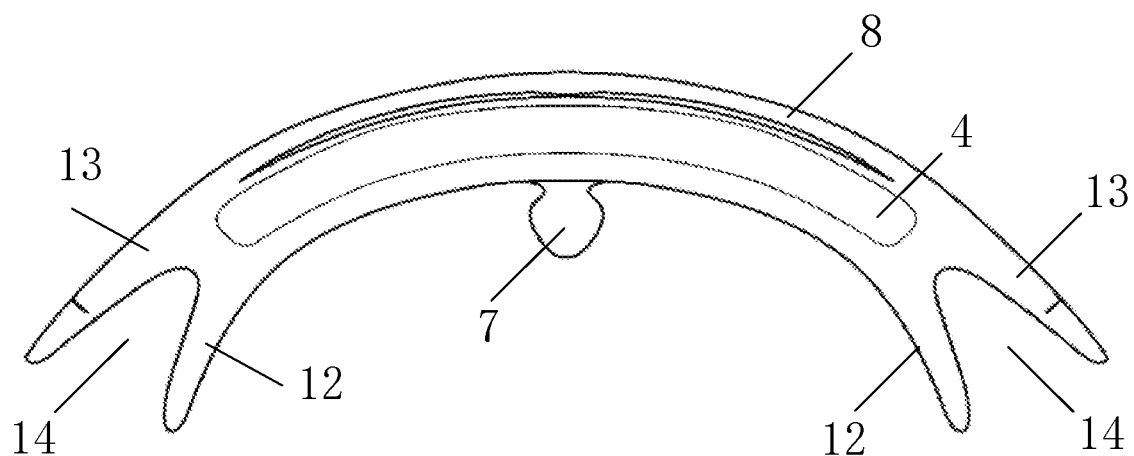
FIG. 3 is a top view of the vocalization appliance for assisting the vocal cord closure training as shown in FIG. 1.
Figure 4:
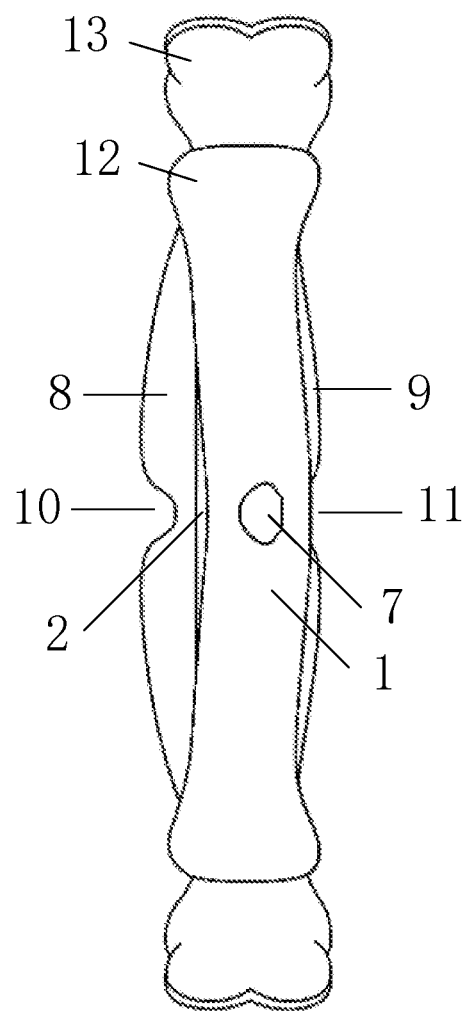
FIG. 4 is a back view of the vocalization appliance for assisting the vocal cord closure training as shown in FIG. 1.

FIG. 1 is a sketch view of a vocalization appliance for assisting vocal cord closure training according to an embodiment of the present invention; FIG. 2 is a front view of the vocalization appliance for assisting vocal cord closure training as shown in FIG. 1; FIG. 3 is a top view of the vocalization appliance for assisting vocal cord closure training as shown in FIG. 1; and FIG. 4 is a back view of the vocalization appliance for assisting vocal cord closure training as shown in FIG. 1. Referring to FIGS. 1-4, a vocalization appliance for assisting vocal cord closure training comprises: an inner arc plate 1, an outer arc plate 2, and two partitions 3 which are oppositely disposed, The vocalization appliance comprises: the inner arc plate 1, the outer arc plate 2, and the two partitions 3 which are oppositely disposed, wherein the inner arc plate 1 is opposite to the outer arc plate 2, and the two partitions 3 are placed with an interval between the inner arc plate 1 and the outer arc plate 2; the two partitions 3, the inner arc plate 1 and the outer arc plate 2 are enclosed to form an accommodating cavity 4, and the accommodating cavity 4 is separated into an upper accommodating room 5 and a lower accommodating room 6 along a height direction; the upper accommodating room 5 accommodates upper incisors 15 while the lower accommodating room 6 accommodates lower incisors 15 (see FIGS. 5a and 5b); opposite side ends of the inner arc plate 1 respectively extend away from the accommodating cavity 4, and opposite side ends of the outer arc plate 2 also respectively extend away from the accommodating cavity 4, thereby separating mouth corners.

In practice, the vocalization appliance is placed in the oral cavity, and the upper incisors 15 and the lower incisors 15 bite into the upper accommodating room 5 and the lower accommodating room 6 respectively, so as to be fixed. The inner arc plate 1 is attached to the inner surface of the teeth, and the opposite side ends of the inner arc plate 1 respectively extend away from the accommodating cavity 4 to separate an upper lip 19 and a lower lip 20; the outer arc plate 2 extends to the outside of the lip, and the opposite side ends of the outer arc plate 2 respectively extend away from the accommodating cavity 4 to keep separating the mouth. By using the above-described vocalization appliance for assisting the vocal cord closure training, the upper accommodating room 5 and the lower accommodating room 6 respectively fix the upper incisors 15 and the lower incisors 15 to leave a certain interval therebetween. Meanwhile, both ends of the inner arc plate 1 and the outer arc plate 2 extend outwards, and the outer arc plate 2 extends from inside of the lip to the outside of the lip to keep separating the mouth corners, so as to increase a distance between the opposite sides of the mouth, increase resonance and promote passive and healthy closure of the vocal cords; as a result, the muscles and nerves, that help the vocal cords close, can be maximally stretched and exercised, which helps to achieve healthy pronunciation In the embodiment, an arc of the inner arc plate 1 is designed according to an arc shape of the inner surface of the teeth, and an arc of the outer arc plate 2 is designed according to an arc shape of the outer surface of the teeth. The inner arc plate 1 and the outer arc plate 2 are oppositely arranged to simultaneously fix the upper teeth and the lower teeth. Accommodation space of the upper accommodating room 5 and the lower accommodating room 6 can be set according to teeth conditions of specific users. Generally, the incisors can include 4 incisors or additional 1 or 2 canines, which are accommodated inside the accommodating cavity. The opposite side ends of the inner arc plate 1 respectively extend toward the canines on both sides; usually extending to the second canine; the opposite side ends of the outer arc plate 2 respectively extend toward the molars at both sides, usually extending to the first molar.

The above-mentioned vocalization appliance for assisting the vocal cord closure training is suitable for singers, voice workers and actors who need to achieve and maintain high level of vocal ability; suitable for patients with vocal dysfunction and patients who need to resume normal vocalization after surgery; and suitable for vocal actors, teachers, speech therapists, patients with vocal dysfunction, patients with vocal diseases, and people with vocal dysfunction due to no or incomplete vocal cord closure. In particular, the present invention is suitable for patients with vocal dysfunctions caused by vocal cord closure, such as vocal cord paralysis, lack of vocal cord closure ability, and poor vocal cord closure.

Preferably, the vocalization appliance further comprises: a tongue depressor 7 disposed on a side surface of the inner arc plate 1 facing away from the outer arc plate 2, wherein the tongue depressor 7 extends away from the outer arc plate 2. When the upper accommodating room 5 and the lower accommodating room 6 respectively fix the upper incisors 15 and the lower incisors 15, the tongue depressor 7 presses against a tongue 18, wherein tongue muscles are passively moved and relatively relaxed to avoid tension and up-warping of the tongue 18 and tension of laryngeal muscle, so that the tongue is better placed while muscles and nerves for closing the vocal cords can work actively to a maximum extent, thereby promoting the passive and healthy closure of the vocal cords and helping to achieve healthy pronunciation and voice resonance.

Preferably, a width of the tongue depressor 7 gradually increases towards the inner arc plate 1. With gradual width change of the tongue depressor 7, a tongue tip is guide along the tongue depressor 7 until it presses against the inner arc plate 1, thereby effectively guiding the tongue 18 to be placed.

Preferably, the tongue depressor 7 comprises a connected end and a free end which are oppositely disposed, wherein the connected end is disposed on the inner arc plate 1 opposite to the lower accommodating room 6, and the free end extends towards the upper accommodating room 5. The tongue depressor 7 is connected to a low position of the inner arc plate 1 through the connected end, and the free end extends obliquely upward to effectively press the tongue 18 to prevent the tongue 18 from being up-warped and prevent the laryngeal muscles from being strained.

In the embodiment, a cross-section of the tongue depressor 7 is approximately leaf-like, wherein the width of the tongue depressor 7 gradually increases from the free end to the connected end, and a thickness of the tongue depressor 7 gradually increases from the free end to the connected end. The tongue depressor 7 and the inner arc plate 1 above it form an acute angle, and the tongue depressor 7 and the inner arc plate 1 below it form an obtuse angle. A distance between the connected end and the upper end surface of the inner arc plate 1 is greater than that between the connected end and the lower end surface of the inner arc plate 1; and a distance between the free end and the upper end surface of the inner arc plate 1 is less than or equal to that between the free end and the lower end surface of the inner arc plate 1. An edge of the tongue depressor 7 is a smooth curve to avoid cutting the tongue 18.

Figure 5A:
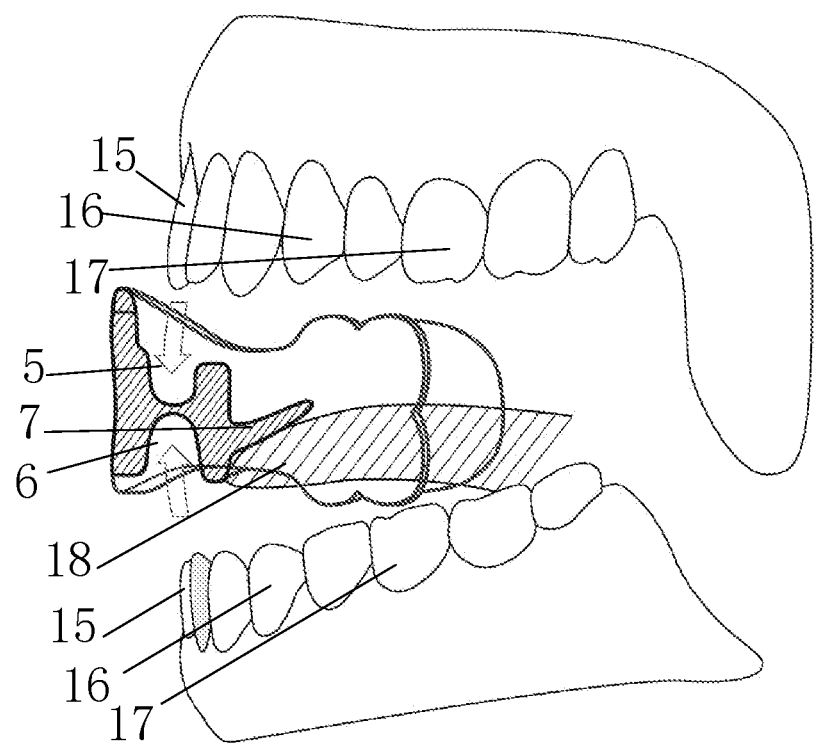
FIGS. 5a-5b are sketch views of the vocalization appliance for assisting the vocal cord closure training as shown in FIG. 1 in use.
Figure 5B:
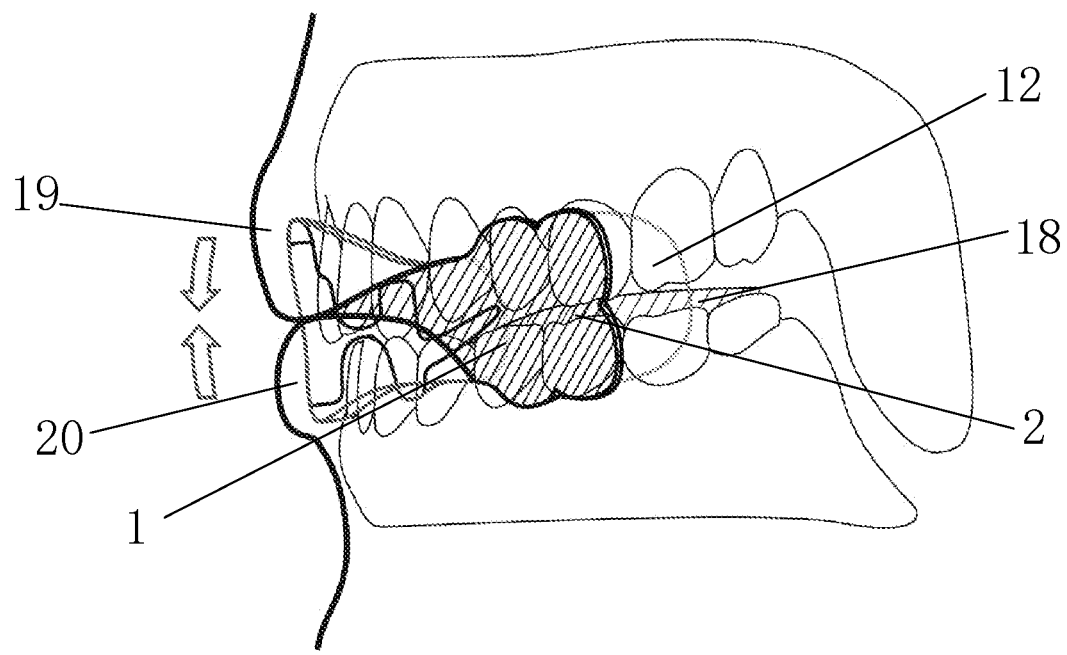

Preferably, an upper end surface of the outer arc plate 2 extends upwardly to form an upper baffle 8, and a lower end surface of the outer arc plate 2 extends downwardly to form a lower baffle 9; the upper baffle 8 prevent an inner surface of an upper lip 19 from contacting upper teeth, and the lower baffle 9 prevents an inner surface of a lower lip 20 from contacting lower teeth (see FIGS. 5a and 5b). When the vocalization appliance is placed in the oral cavity, the upper baffle 8 is located between the inner surface of the upper lip 19 and the outer surface of the upper teeth, and the lower baffle 9 is located between the inner surface of the lower lip 20 and the outer surface of the lower teeth, so as to provide a barrier function and respectively support the upper lip 19 and the lower lip 20, so that the mouth corners are opened.

In the embodiment, the upper baffle 8, a plate body of the outer arc plate 2, and the lower baffle 9 are integrally formed.

Preferably, an upper groove 10 for accommodating an upper lip ligament is provided at a middle of the upper baffle 8, and the upper baffle 8 smoothly transitions from opposite sidewalls of the upper groove 10 to the upper end face at both sides; a lower groove 11 for accommodating a lower lip ligament is provided at a middle of the lower baffle 9, and the lower baffle 9 smoothly transitions from opposite sidewalls of the lower groove 11 to the lower end face at both sides. When the vocalization appliance is placed in the oral cavity, the upper baffle 8 is located between the inner surface of the upper lip 19 and the outer surface of the upper teeth, and the upper lip ligament is located in the upper groove 10; the lower baffle 9 is located between the inner surface of the lower lip 20 and the outer surface of the lower teeth, and the lower lip ligament is located in the lower groove 11. Therefore, connection stability of the vocalization appliance in the oral cavity is improved. The upper baffle 8 is respectively directed from the opposite side walls of the upper recess 10 The upper baffle 8 smoothly transitions from the opposite sidewalls of the upper groove 10 to the upper end face at both sides, and the lower baffle 9 smoothly transitions from opposite sidewalls of the lower groove 11 to the lower end face at both sides, so as to conform to human body mechanics and improve comfort.

In the embodiment, edge shapes of both the upper baffle 8 and the lower baffle 9 are designed according to lip shapes of the user. Generally, the upper baffle 8 and the lower baffle 9 have different structures, and a height of the upper baffle 8 is slightly larger than a height of the lower baffle 9. The upper baffle 8 has a symmetrical structure along a center line of the upper groove 10, and the lower baffle 9 has a symmetrical structure along a center line of the lower groove 11. A groove width of the upper groove 10 is slightly smaller that of the lower groove 11, and a groove depth of the upper groove 10 is slightly larger than that of the lower groove 11.

Preferably, both end portions of the inner arc plate 1 are first end portions 12, and the first end portions 12 extend from a joint of the inner arc plate 1 and the partitions 3 towards canines 16 (see FIGS. 5a and 5b); both end portions of the outer arc plate 2 are second end portions 13, and the second end portions 13 extend from a joint of the outer arc plate 2 and the partitions 3 towards molars 17 (see FIGS. 5a and 5b). The first end portions 12 increase ductility of the inner arc plate 1 in the oral cavity, and the second end portions 13 increase ductility of the outer arc plate 2 outside the mouth, so as to effectively support and separate the mouth corners, increase a distance between opposite sides of the oral cavity, and increase the resonance, in such a manner that the muscles and nerves helping to close the vocal cords can work actively to a maximum extent, thereby promoting the passive and healthy closure of the vocal cords and helping to achieve healthy pronunciation and voice resonance.

Preferably, gaps 14 are reserved between the first end portions 12 of the inner arc plate 1 and the second end portions 13 of the outer arc plate 2, and widths of the gaps 14 gradually increase backwards the accommodating cavity 4. The first end portions 12 extend along a tooth arrangement direction to support and an inner side of the lip, and the second end portions 13 extend to the outside of the lip to effectively keep separate the mouth corners by the second end portions 13. The gaps 14 helps the second end portions 13 to extend from the inside to the outside, wherein the gradually changed gaps 14 reduce difficulty of disassembly and assembly, while ensuring that both the first end portions 12 and the second end portions 13 can provide effective support.

In the embodiment, widths of the first end portions 12 are slightly larger than a width of a plate body of the inner arc plate 1; and widths of the second end portions 13 are greater than a width of the plate body of the outer arc plate 2.

Preferably, each of the first end portions 12 of the inner arc plate 1 comprises a first upper side surface, a first end surface, and a first lower side surface, wherein smooth transition is provided between the first upper side surface, the first end surface, and the first lower side surface; each of the second end portions 13 of the outer arc plate 2 comprises a second upper side surface, a second end surface, and a second lower side surface, wherein smooth transition is provided between the second upper side surface, the second end surface, and the second lower side surface; slits are respectively provided at a middle of the second upper side, a middle of the second end surface, and a middle of the second lower side. The first end portion 12 has a smooth transition from the first upper side surface through the first end surface to the first lower side surface; so as to provide good support for the inner surface of the upper lip 19 and the inner surface of the lower lip 20 to improve comfort. The end portion 13 has a smooth transition from the second upper side through the second end surface to the second lower side, so as to provide good support for the upper lip 19 and the lower lip 20 to improve comfort. The slits are respectively provided at the middle of the second upper side, the middle of the second end surface, and the middle of the second lower side to provide a relatively relaxed space for the lip to passively move the lip.

Furthermore, preferably, the vocalization appliance is made of a rubber foam material. Ethylene-vinyl acetate copolymer (EVA) has good elasticity, flexibility and transparency, and can meet the requirements of medical non-toxic, high temperature and low temperature resistance. Therefore, it is suitable for making medical equipment.

In the embodiment, the vocalization appliance for assisting the vocal cord closure training is integrally formed, thereby improving structural strength so that it can be used multiple times for a long time. Moreover, the use of EVA material can provide certain flexibility. Usually, the user can wear the vocalization appliance in less than 5 seconds without causing any side effects such as blocking airways, blocking esophagus and obstructing breathing.

In order to further understand vocalization, the vocalization appliance may be equipped with a sound sensor, and the sound sensor is connected with an external computer. When the user places the vocalization appliance into the oral cavity, the sound sensor collects data and transmits the data to the external computer during vocalization, in such a manner that user vocalization can be collected and analyzed in real time to improve treatment efficiency and accuracy.

Use of the vocalization appliance for assisting the vocal cord closure training will be further described below. FIGS. 5a-5b sketch views of the vocalization appliance for assisting the vocal cord closure training as shown in FIG. 1 in use.

As shown in FIG. 5a and FIG. 5b, the vocalization appliance is placed in the oral cavity, and the upper incisors 15 and the lower incisors 15 bite into the upper accommodating room 5 and the lower accommodating room 6 respectively, so as to be fixed. The tongue depressor 7 presses against a tongue 18, wherein tongue muscles are passively moved and relatively relaxed to avoid tension and up-warping of the tongue 18 and tension of laryngeal muscle. The inner arc plate 1 is attached to the inner surface of the teeth, and the first ends 12 of the opposite sides of the inner arc plate 1 respectively extend to the canines 16 to separate the upper lip 19 and the lower lip 20. When the upper baffle 8 is located between the inner surface of the upper lip 19 and the outer surface of the upper teeth, the upper lip ligament is located in the upper groove 10; when the lower baffle 9 is located between the inner surface of the lower lip 20 and the outer surface of the lower teeth, and the lower lip ligament is located in the lower groove 11. The outer arc plate 2 extends to the outside of the lips, and the second end portions 13 of the opposite sides of the outer arc plate 2 respectively extend to the molars 17 to keep separating the mouth corners.

It can be seen from the above description and practice that the vocalization appliance for assisting vocal cord closure training of the present invention has the following advantages compared with the prior art: the upper accommodating room and the lower accommodating room respectively fix the upper incisors and the lower incisors, so that an interval is maintained between the upper teeth and the lower teeth; the opposite ends of the inner arc plate and the opposite ends of the outer arc plate all extend away from the accommodating cavity for separating the upper lip from the lower lip, and keeping the lips and muscles relaxed; increasing a distance between the opposite sides of the mouth helps to increase resonance and promote passive and healthy closure of the vocal cords; as a result, the muscles and nerves, that help the vocal cords close, can be maximally stretched and exercised, which helps to achieve healthy pronunciation, fully resonate sinus and frontal sinus, and produce a voice resonance; the outer arc plate extends from inside of the lips to outside of the lips to keep separating the mouth corners, while avoid a bad habit of actively opening the mouth during vocalization.

Those skilled in the art would understand that the above description is only the specific embodiments of the present invention, and is not intended to be limiting. Any modifications, equivalents, improvements, etc., made within the spirit of the present invention, should be included in the scope of protection of the present invention.

What is claimed is:

1. A vocalization appliance for assisting vocal cord closure training, comprising: an inner arc plate, an outer arc plate, and two partitions which are oppositely disposed, wherein the inner arc plate is opposite to the outer arc plate, and the two partitions are placed with an interval between the inner arc plate and the outer arc plate; the two partitions, the inner arc plate and the outer arc plate are enclosed to form an accommodating cavity, and the accommodating cavity is separated into an upper accommodating room and a lower accommodating room along a height direction; the upper accommodating room accommodates upper incisors while the lower accommodating room accommodates lower incisors; opposite side ends of the inner arc plate respectively extend away from the accommodating cavity, and opposite side ends of the outer arc plate also respectively extend away from the accommodating cavity, thereby separating mouth corners.

2. The vocalization appliance, as recited in claim 1, further comprising: a tongue depressor disposed on a side surface of the inner arc plate facing away from the outer arc plate, wherein the tongue depressor extends away from the outer arc plate.

3. The vocalization appliance, as recited in claim 2, wherein a width of the tongue depressor gradually increases towards the inner arc plate.

4. The vocalization appliance, as recited in claim 3, wherein the tongue depressor comprises a connected end and a free end which are oppositely disposed, wherein the connected end is disposed on the inner arc plate opposite to the lower accommodating room, and the free end extends towards the upper accommodating room.

5. The vocalization appliance, as recited in claim 3, wherein an upper end surface of the outer arc plate extends upwardly to form an upper baffle, and a lower end surface of the outer arc plate extends downwardly to form a lower baffle; the upper baffle prevent an inner surface of an upper lip from contacting upper teeth, and the lower baffle prevents an inner surface of a lower lip from contacting lower teeth.

6. The vocalization appliance, as recited in claim 5, wherein an upper groove for accommodating an upper lip ligament is provided at a middle of the upper baffle, and the upper baffle smoothly transitions from opposite sidewalls of the upper groove to the upper end face at both sides; a lower groove for accommodating a lower lip ligament is provided at a middle of the lower baffle, and the lower baffle smoothly transitions from opposite sidewalls of the lower groove to the lower end face at both sides.

7. The vocalization appliance, as recited in claim 3, wherein both end portions of the inner arc plate are first end portions, and the first end portions extend from a joint of the inner arc plate and the partitions towards canines; both end portions of the outer arc plate are second end portions, and the second end portions extend from a joint of the outer arc plate and the partitions towards molars.

8. The vocalization appliance, as recited in claim 7, wherein gaps are reserved between the first end portions of the inner arc plate and the second end portions of the outer arc plate, and widths of the gaps gradually increase backwards the accommodating cavity.

9. The vocalization appliance, as recited in claim 8, wherein each of the first end portions of the inner arc plate comprises a first upper side surface, a first end surface, and a first lower side surface, wherein smooth transition is provided between the first upper side surface, the first end surface, and the first lower side surface; each of the second end portions of the outer arc plate comprises a second upper side surface, a second end surface, and a second lower side surface, wherein smooth transition is provided between the second upper side surface, the second end surface, and the second lower side surface; slits are respectively provided at a middle of the second upper side, a middle of the second end surface, and a middle of the second lower side.

10. The vocalization appliance, as recited in claim 3, wherein the vocalization appliance is made of a rubber foam material.

11. The vocalization appliance, as recited in claim 2, wherein the tongue depressor comprises a connected end and a free end which are oppositely disposed, wherein the connected end is disposed on the inner arc plate opposite to the lower accommodating room, and the free end extends towards the upper accommodating room.

12. The vocalization appliance, as recited in claim 2, wherein an upper end surface of the outer arc plate extends upwardly to form an upper baffle, and a lower end surface of the outer arc plate extends downwardly to form a lower baffle; the upper baffle prevent an inner surface of an upper lip from contacting upper teeth, and the lower baffle prevents an inner surface of a lower lip from contacting lower teeth.

13. The vocalization appliance, as recited in claim 12, wherein an upper groove for accommodating an upper lip ligament is provided at a middle of the upper baffle, and the upper baffle smoothly transitions from opposite sidewalls of the upper groove to the upper end face at both sides; a lower groove for accommodating a lower lip ligament is provided at a middle of the lower baffle, and the lower baffle smoothly transitions from opposite sidewalls of the lower groove to the lower end face at both sides.

14. The vocalization appliance, as recited in claim 2, wherein both end portions of the inner arc plate are first end portions, and the first end portions extend from a joint of the inner arc plate and the partitions towards canines; both end portions of the outer arc plate are second end portions, and the second end portions extend from a joint of the outer arc plate and the partitions towards molars.

15. The vocalization appliance, as recited in claim 14, wherein gaps are reserved between the first end portions of the inner arc plate and the second end portions of the outer arc plate, and widths of the gaps gradually increase backwards the accommodating cavity.

16. The vocalization appliance, as recited in claim 15, wherein each of the first end portions of the inner arc plate comprises a first upper side surface, a first end surface, and a first lower side surface, wherein smooth transition is provided between the first upper side surface, the first end surface, and the first lower side surface; each of the second end portions of the outer arc plate comprises a second upper side surface, a second end surface, and a second lower side surface, wherein smooth transition is provided between the second upper side surface, the second end surface, and the second lower side surface; slits are respectively provided at a middle of the second upper side, a middle of the second end surface, and a middle of the second lower side.

17. The vocalization appliance, as recited in claim 2, wherein the vocalization appliance is made of a rubber foam material.

18. The vocalization appliance, as recited in claim 1, wherein an upper end surface of the outer arc plate extends upwardly to form an upper baffle, and a lower end surface of the outer arc plate extends downwardly to form a lower baffle; the upper baffle prevent an inner surface of an upper lip from contacting upper teeth, and the lower baffle prevents an inner surface of a lower lip from contacting lower teeth.

19. The vocalization appliance, as recited in claim 18, wherein an upper groove for accommodating an upper lip ligament is provided at a middle of the upper baffle, and the upper baffle smoothly transitions from opposite sidewalls of the upper groove to the upper end face at both sides; a lower groove for accommodating a lower lip ligament is provided at a middle of the lower baffle, and the lower baffle smoothly transitions from opposite sidewalls of the lower groove to the lower end face at both sides.

20. The vocalization appliance, as recited in claim 1, wherein both end portions of the inner arc plate are first end portions, and the first end portions extend from a joint of the inner arc plate and the partitions towards canines; both end portions of the outer arc plate are second end portions, and the second end portions extend from a joint of the outer arc plate and the partitions towards molars.

21. The vocalization appliance, as recited in claim 20, wherein gaps are reserved between the first end portions of the inner arc plate and the second end portions of the outer arc plate, and widths of the gaps gradually increase backwards the accommodating cavity.

22. The vocalization appliance, as recited in claim 21, wherein each of the first end portions of the inner arc plate comprises a first upper side surface, a first end surface, and a first lower side surface, wherein smooth transition is provided between the first upper side surface, the first end surface, and the first lower side surface; each of the second end portions of the outer arc plate comprises a second upper side surface, a second end surface, and a second lower side surface, wherein smooth transition is provided between the second upper side surface, the second end surface, and the second lower side surface; slits are respectively provided at a middle of the second upper side, a middle of the second end surface, and a middle of the second lower side.

23. The vocalization appliance, as recited in claim 1, wherein the vocalization appliance is made of a rubber foam material.

\* \* \* \* \*